United States Patent
Narine et al.

(10) Patent No.: US 9,637,698 B2
(45) Date of Patent: May 2, 2017

(54) CERTAIN DIMERS AS CRYSTALLIZATION DEPRESSANTS

(71) Applicant: Trent University, Peterborough (CA)

(72) Inventors: Suresh Narine, Peterborough (CA); Laziz Bouzidi, Peterborough (CA); Bruce Darling, Peterborough (CA); Mark Baker, Peterborough (CA); Shaojun Li, Peterborough (CA); Ali Mahdevari, Peterborough (CA)

(73) Assignee: Trent University, Peterborough, Ontario (CA)

( * ) Notice: Subject to any disclaimer, the term of this patent is extended or adjusted under 35 U.S.C. 154(b) by 397 days.

(21) Appl. No.: 14/209,505

(22) Filed: Mar. 13, 2014

(65) Prior Publication Data

US 2014/0325899 A1 Nov. 6, 2014

Related U.S. Application Data

(60) Provisional application No. 61/798,974, filed on Mar. 15, 2013.

(51) Int. Cl.
*C10L 1/00* (2006.01)
*C10L 10/14* (2006.01)
*C10L 1/19* (2006.01)
*C07C 69/593* (2006.01)

(52) U.S. Cl.
CPC ............ *C10L 10/14* (2013.01); *C07C 69/593* (2013.01); *C10L 1/1915* (2013.01); *C10L 2200/0476* (2013.01)

(58) Field of Classification Search
CPC .............. C10L 10/14; C10L 1/1915; C10L 2200/0476; C07C 69/593
See application file for complete search history.

(56) References Cited

U.S. PATENT DOCUMENTS

2012/0255222 A1 10/2012 DiBiase et al.

FOREIGN PATENT DOCUMENTS

WO WO 2012/021959 A1 2/2012
WO WO 2013/156872 A2 10/2013

OTHER PUBLICATIONS

Hernqvist, L. Polymorphism of Triglycerides a Crystallographic Review, Food Structure: vol. 9:No. 1, Article 5 (1990).*
Li, etal. Synthesis and Physical Properties of Triacylglycerol Oligomers: Examining the Physical Functionality Potential of Self-Metathesized Highly Unsaturated Vegetable Oils, Ind. Eng. Chem. Res. vol. 52, pp. 2209-2219 (2013).*

(Continued)

*Primary Examiner* — Cephia D Toomer
(74) *Attorney, Agent, or Firm* — Bereskin & Parr LLP/S.E.N.C.R.L., s.r.l.; Michael Fenwick

(57) ABSTRACT

This application relates to certain dimers as crystallization depressants for biodiesel fuels, and methods for making the same. Such dimers, due to their particular structure and conformation, disrupt the regular packing of linear saturated fatty acid methyl esters, thereby delaying nucleation and mitigating crystal growth. In some embodiments, the dimer includes (E)-1-(1-(oleoyloxy)-3-(stearoyloxy)propan-2-yl) 18-(1-(oleoyloxy)-3-(stearoyloxy)propan-2-yl)octadec-9-enedioate.

11 Claims, 10 Drawing Sheets

(56) References Cited

OTHER PUBLICATIONS

International Search Report and Written Opinion of the International Searching Authority issued in PCT Patent Application No. PCT/CA2014/050238, mailed Jun. 10, 2014, 9 pages.
Li, Shojun; Hojabri, Leila; and Narine, Suresh S. Controlling Product Composition of Metathesized Triolein by Reaction Concentrations. J. Am. Oil Chem. Soc. (2012) 892077-2069. (Listed in the European Search Report copy enclosed).

* cited by examiner

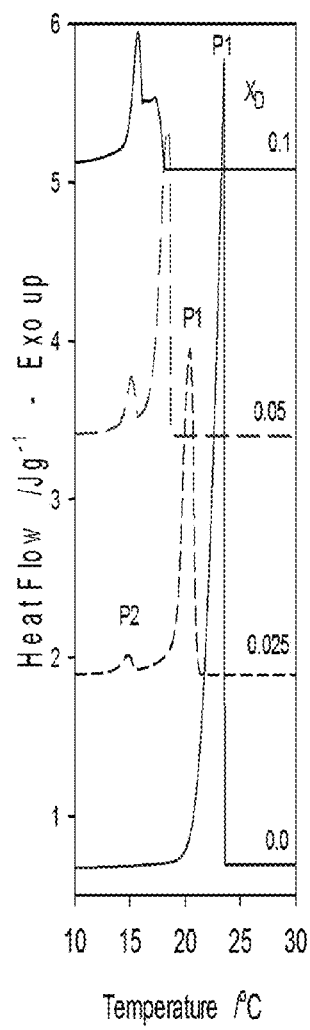
Fig. 2A1
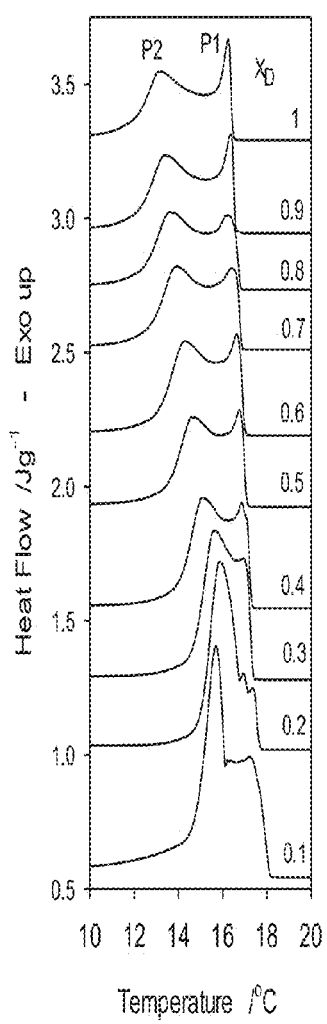
Fig. 2A2
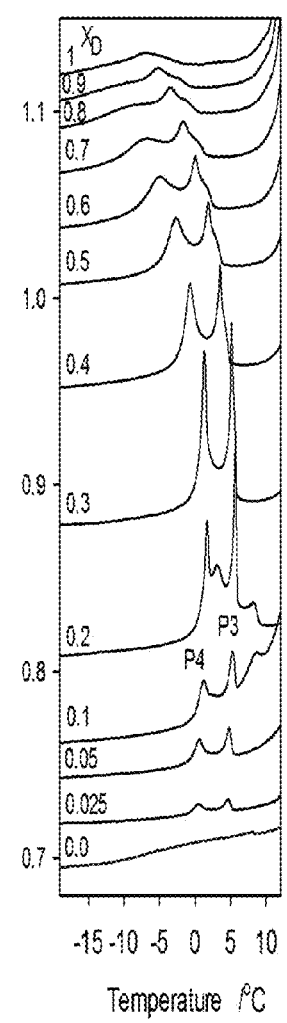
Fig. 2A3

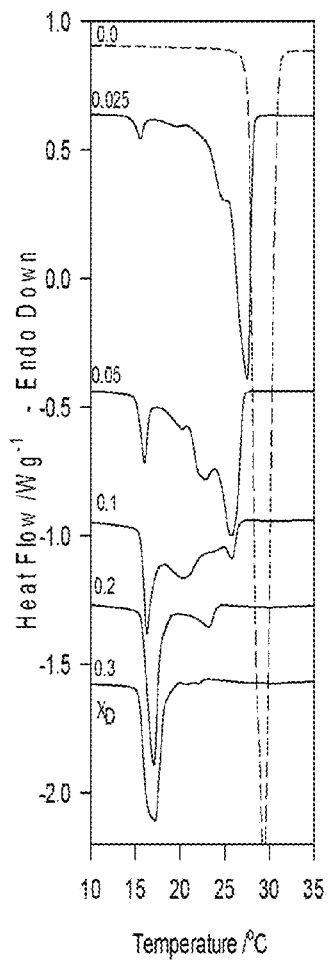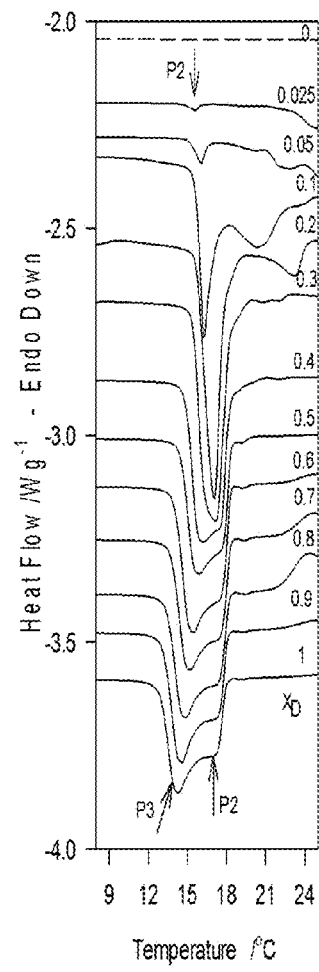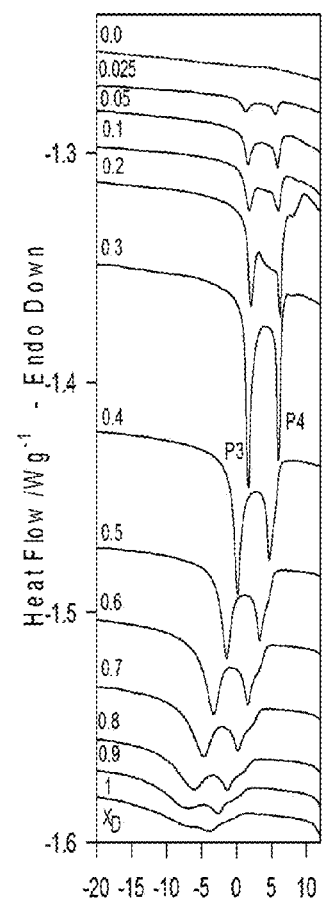
Fig. 3A1  Fig. 3A2  Fig. 3A3

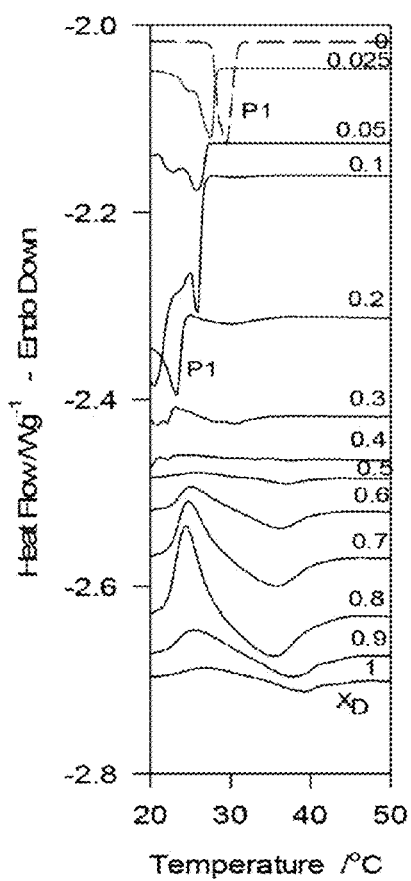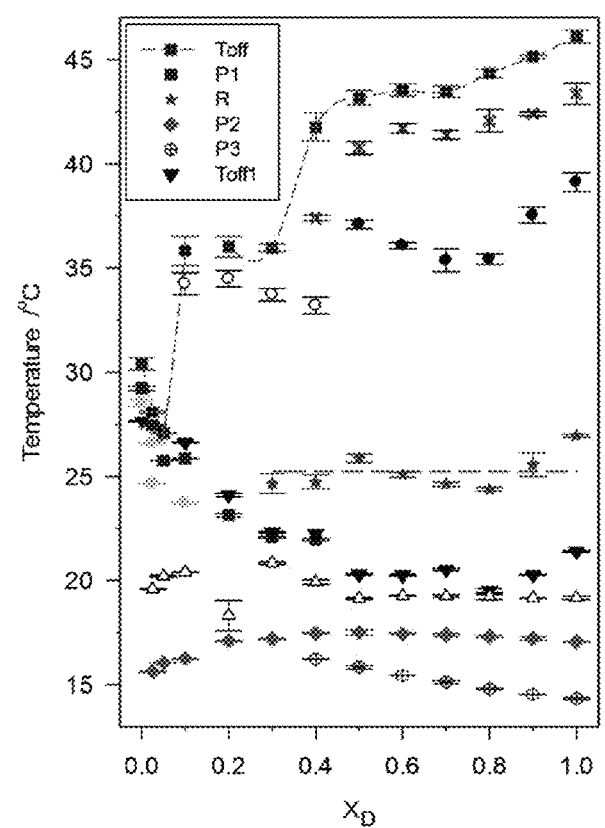
Fig. 3A4                    Fig. 3B

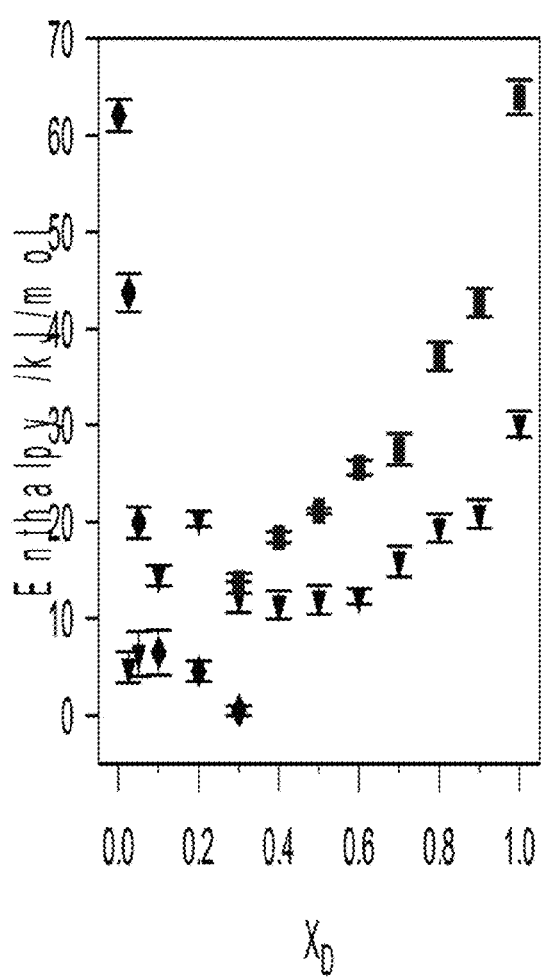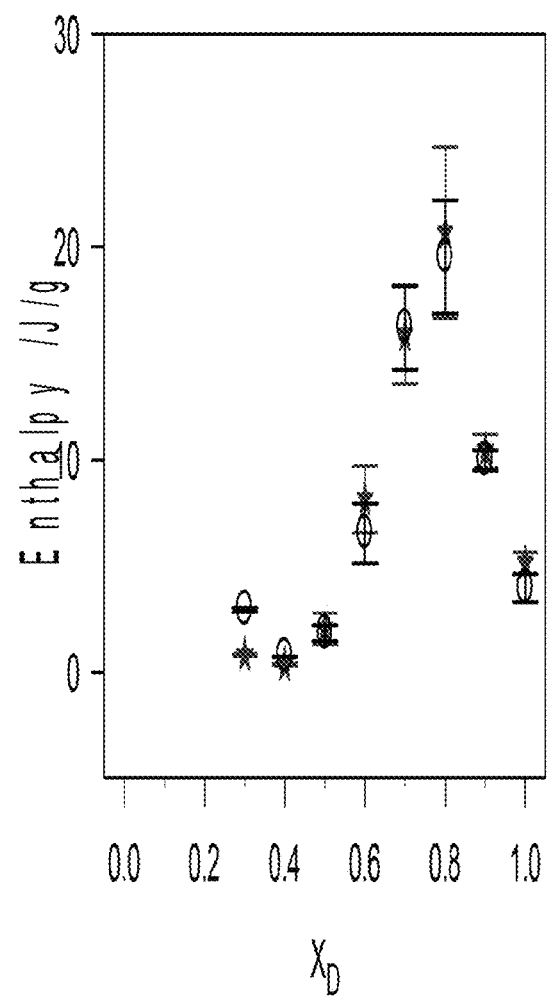
Fig. 3C
Fig. 3D

D at -60 °C
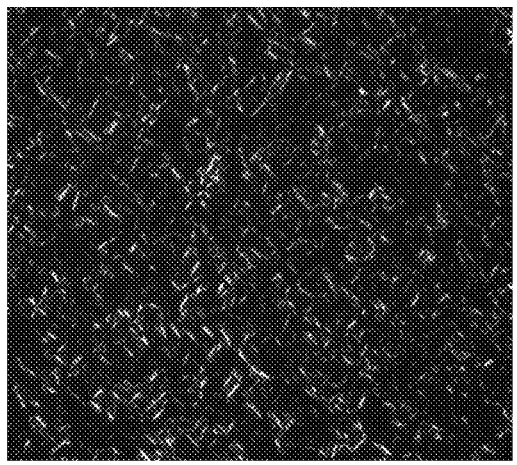
0.10$_D$ at -60 °C
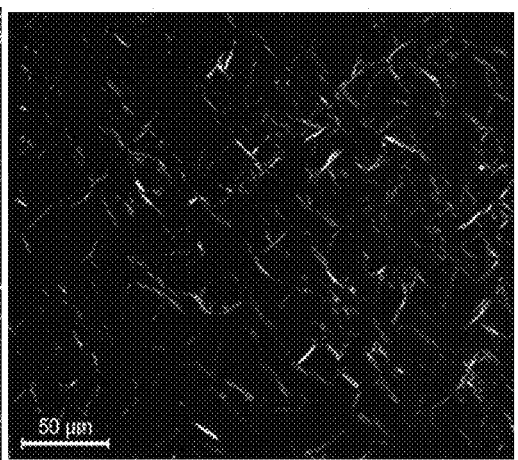
Fig. 4A
Fig. 4B
0.05$_D$ at -60 °C
MeP at -10 °C
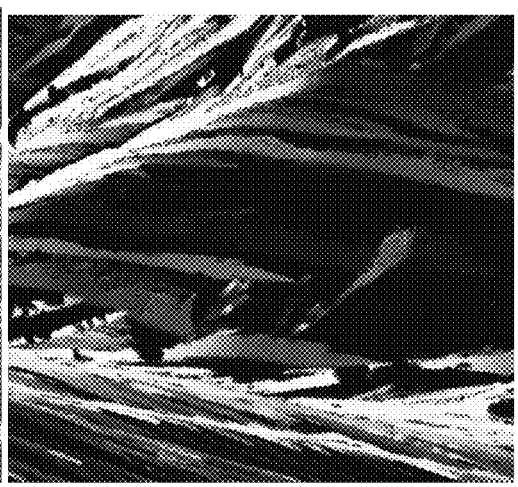
Fig. 4C
Fig. 4D

CERTAIN DIMERS AS CRYSTALLIZATION DEPRESSANTS

CROSS REFERENCE TO RELATED APPLICATIONS

A claim of priority for this application under 35 U.S.C.§119(e) is hereby made to the following U.S. provisional patent application: U.S. Ser. No. 61/798,974 filed Mar. 15, 2013; and this application is incorporated herein by reference in its entirety.

FIELD OF THE INVENTION

This application relates to certain dimers as crystallization depressants, and methods for making the same.

BACKGROUND OF THE INVENTION

Diesel fuels and/or biodiesel fuels typically contain wax, and when subjected to low temperatures, these fuels often undergo wax crystallization, gelling and/or viscosity increase. This reduces the ability of the fuel to flow and creates filter plugging which adversely affects the operability of vehicles using these fuels. Flow improvers have been used to modify the wax structure as it builds during cooling. These additives are typically used to keep the wax crystals small so that they can pass through fuel filters. Also, pour point dispersants are sometimes used in diesel fuel to ensure that it can be pumped at low temperatures.

Due to environmental concerns and the decline of known petroleum reserves with subsequent price increases of petroleum, biodiesel fuels are becoming a focus of intense research and development efforts. Biodiesel fuels typically comprise fatty acid esters, prepared for example by transesterifying triglycerides with lower alcohols, e.g. methanol or ethanol. A typical biodiesel fuel is the fatty acid ester of a natural oil (i.e. rapeseed oil or of soybean oil, as non-limiting examples). One of the major problems associated with the use of biodiesel is its poor cold flow properties resulting from crystallization of saturated fatty compounds in cold conditions, as indicated by its relatively high cloud points (CP) and pour points (PP). A 20° C. reduction in cold filter plugging point is necessary for some biodiesel fuels to find utility in colder climates such as those of North America and Europe in winter.

Several efforts to mitigate the low-temperature problems of biodiesel have been investigated over the past several years. Many popular approaches have included blending biodiesel with conventional diesel fuel, winterization, and use of synthetic additives. Also, studies have been performed to show the diversification in the feedstock and genetic modification of the feedstock, aimed to provide a reduction in the saturated content of the fatty acid methyl esters (FAME) in biodiesel as well as modification of FAME composition/profile of the fuels. While there have been efforts to create additives that may reduce the PP and cold filter plugging point (CFPP) of fuels, many are not cost effective. Also, increasing the unsaturated content of biodiesel may improve its cold flow properties, but also leads to the alteration of the oxidative stability of the fuel. The overall thermal behavior of biodiesel is affected by the relative concentration of its saturated and unsaturated FAME components. The cold flow issue is primarily a multifaceted problem of crystallization (of saturated FAMEs) in solution (unsaturated FAMEs) which can be approached from several angles.

Several approaches have been utilized to lower the onset temperature of crystallization of biodiesel, targeting particularly the saturated FAMEs such as methyl palmitate (MeP) and methyl stearate (MeS), which influence most its flow behavior at low temperature. The most popular approach is the use of crystallization depressant additives.

Saturated triacylglycerols (TAGs) and dimers of TAGs, particularly those having two double bonds at the sn-1 and sn-3 positions, have been found to be effective in suppressing the crystallization of FAMEs. One structured triacylglycerol dimer, (E)-1-(1-(oleoyloxy)-3-(stearoyloxy)propan-2-yl) 18-(1-(oleoyloxy)-3-(stearoyloxy) propan-2-yl) octadec-9-enedioate (Compound D), which can be produced from self-metathesis of natural oils, is one compound that has been found to significantly reduce the crystallization temperature of biodiesel.

BRIEF DESCRIPTION OF THE SEVERAL VIEWS OF THE DRAWINGS

FIGS. 2A1, 2A2, and 2A3 depicts crystallization thermograms of Compound D/MeP mixtures cooled at 1° C./min.

FIGS. 3A1, 3A2, 3A3, and 3A4 depict thermograms of Compound D/MeP mixtures obtained with heating at 1° C./min. The Compound D molar ratio is indicated above each curve.

FIG. 3B depicts the phase diagram obtained using the characteristic transition temperatures obtained during heating.

FIG. 3C depicts the enthalpy of melting of peaks P1 (♦, $\Delta H_1$), P2 (▼, $\Delta H_2$) and P3 (▩, $\Delta H_3$).

FIG. 3D depicts the enthalpy of the recrystallization exotherm (✻) and enthalpy of subsequent endotherms (○) recorded for the Compound D/MeP mixtures.

FIGS. 4A, 4B, 4C, and 4D depict PLM images of fully crystallized Compound D, $0.10_D$, $0.05_D$ mixtures (500×) and MeP (100×) obtained after cooling from the melt at a constant rate of 1 K/min.

DETAILED DESCRIPTION OF THE INVENTION

Figure 1A:
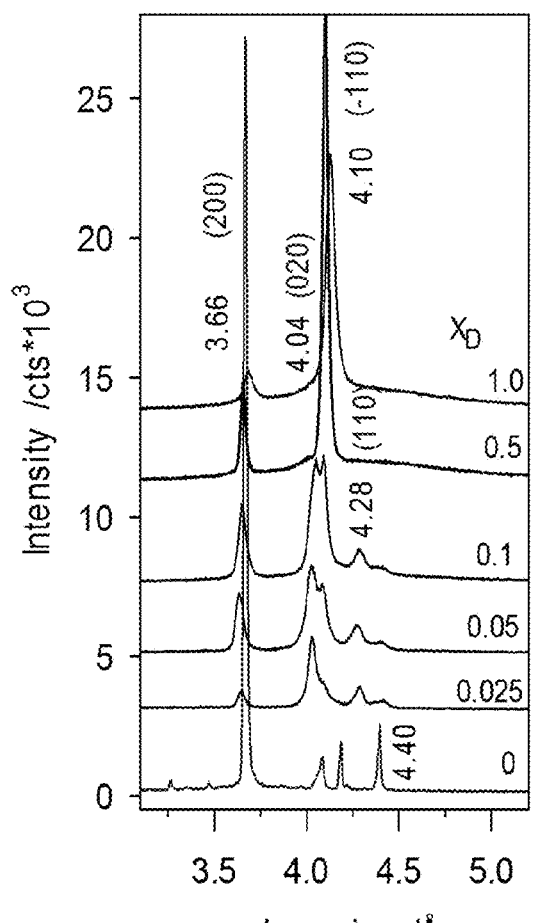
FIGS. 1A and 1B depicts a wide angle x-ray diffraction (WAXD) in 1a and a small angle x-ray diffraction (SAXD) spectra of the mixture with $X_D \leq 0.10$, $0.50_D$ and MeP in 1b.

It is generally known that additives suppress the crystallization of biodiesel and delays the rate of nucleation and/or crystal growth processes. At the nucleation level, additives delay the formation of critical nuclei from embryo clusters through molecular-level interactions between the crystallizing host molecules and the interfering additive molecules. The crystal growth is delayed when the additive prevents the adsorption and incorporation of crystallizing host molecules at the growing crystal surfaces. The additive is most efficient when both length scales are impacted. The disturbance to crystallization is therefore manifested at both the nanostructure and microstructure levels. The changes may be evidenced depending on concentration by specific changes to crystal structure and polymorphism, and microstructure, i.e., fat network and crystal shape and habit.

Polarized Light Microscopy (PLM) is an efficient technique to study the microstructure of lipid systems. The development of fat crystals from the start of crystallization to the complete fat network can be exposed by time/temperature resolved PLM, or thermo-microscopy. The technique also allows access to nucleation parameters when the rate of nucleation is low or the rate of crystal formation (number of crystals per time) is low, i.e., when individual crystals can be individually counted and considered as nuclei.

X-Ray Diffraction (XRD) is a useful tool for studying crystallization at the molecular and nanoscale levels. It allows access to the details of the lamellar packing, as well as the subcell structure of the fat crystals, and provides information on the intermolecular interactions at play during the development of the crystal phases. XRD also provides valuable information on the crystal arrangement, homogeneity and order state at the crystallized domains which are usually at the nanoscale. The technique provides access to the electronic density map which in turn provides an indication of the localization of atoms/group of atoms.

In this application, a model binary system made of methyl palmitate (MeP) and Compound D was investigated using DSC, XRD and PLM. A complex and unusual phase behavior was uncovered for this system. The phase diagram presented an apparent eutectic at approximately 5% of Compound D, followed by three stepped transformation lines indicating three concentration regions of defined phases of increasing stability. The crystal packing as detected by XRD for the solid phases were shown to be guided by the bulky Compound D molecules to form exclusively orthorhombic crystals. The findings are explained by the formation of Compound D/MeP composite units in which the dimer associates with the MeP molecules at its fatty acid branches and bridge levels starting from concentrations as low as 10%. The association forms in the liquid state where the mobility of MeP and free rotation of the Compound D branches are favorable. The disruptive effect of Compound D on the packing of the saturated FAME was effective only at low concentrations (<0.10), because there were not enough Compound D carriers to form the Compound D/MeP units.

It is surmised that the oligomers, because of their particular structure and conformation, disrupt the regular packing of the linear saturated FAMEs, thereby delaying nucleation and mitigating crystal growth. The chemical structure of Compound D is shown in Scheme 1. Compound D which has cis-double bonds in two of its carbon chains is used as a model molecule to study the mechanisms with which it disturbs the packing of a common FAME in biodiesel, namely MeP. Also, we examine the extent to which Compound D can delay nucleation and affect crystal growth and crystal size.

Scheme 1: Structure of (E)-1-(1-(oleoyloxy)-3-(stearoyloxy) propan-2-yl) 18-(1-(oleoyloxy)-3-(stearoyloxy)propan-2-yl) octadec-9-enedioate (Compound D).

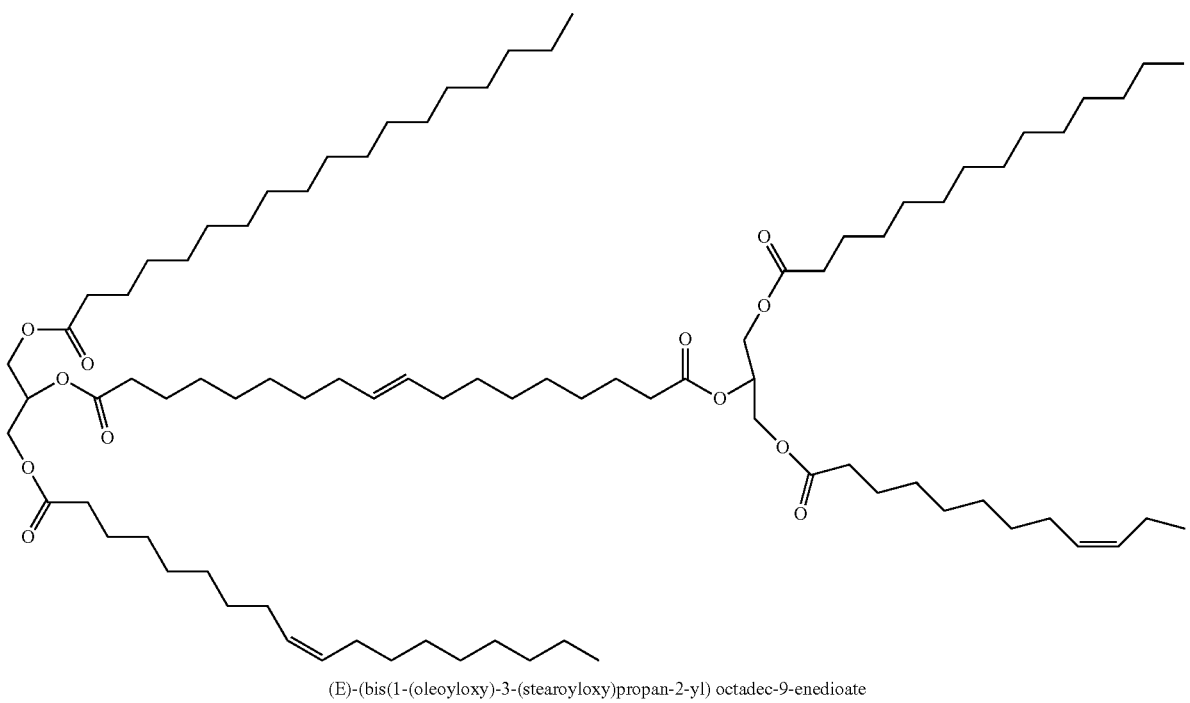

(E)-(bis(1-(oleoyloxy)-3-(stearoyloxy)propan-2-yl) octadec-9-enedioate

The thermal properties of thirteen (13) Compound D/MeP mixtures were investigated using Differential Scanning calorimetry (DSC). Crystal structure and microstructure of selected mixtures were examined by X-Ray Diffraction (XRD) and Polarized Light Microscopy (PLM), respectively, in order to develop a better understanding of the relationship between structure and physical properties.

Materials and Methods of Preparation for Compound D

Materials

Methyl Palmitate (MeP) purchased from Sigma-Aldrich (Oakville, Ontario) at a claimed purity of 96% was further purified in our laboratory to a purity greater than 99%. The purity of MeP was determined by GC-FID. The sample was run as is in chloroform, using a Zebron Capillary GC (ZB-5HT Inferno) Column (Terrance, Calif., USA). D was synthesized with a purity of more than 99%. The purity of Compound D was determined by a Waters Alliance (Milford, Mass.) e2695 HPLC system fitted with a Waters ELSD 2424 evaporative light scattering detector.

Stearoyl chloride (98%), N,N'-dicyclohexylcarbodiimide (DCC), 4-dimethylaminopyridine (DMAP), Grubbs generation II catalyst and sodium borohydride were purchased from Sigma-Aldrich. 2,3-dihydroxypropyl oleate and 1,18-Octadec-9-enedioic acid were prepared. Chloroform was purified by distillation over calcium hydride.

Compound D and MeP were mixed in the desired molar fractions, and then melted and homogenized using a mechanical stirrer. Special care was taken for the overall handling and storage (0° C.) of the samples. The molar fractions, $X_D$, used are 0, 0.025, 0.05, 0.1, 0.2, 0.3, 0.40, 0.50, 0.60, 0.70, 0.80, 0.90 and 1.00.

Analytical Methods—Nuclear Magnetic Resonance ($^1$H and $^{13}$C-NMR)

$^1$H and $^{13}$C-NMR spectra were recorded on a Bruker Advance III 400 spectrometer (Bruker BioSpin MRI GmbH, Karlsruhe, Germany) at a frequency of 400 MHz and 100 MHz respectively, using a 5 mm BBO probe. 1D $^1$H Spectra were acquired at 25° C. over a 16-ppm spectral window with a 1 s recycle delay, 32 transients. 1D $^{13}$C spectra were acquired at 25° C. over a 240-ppm spectral window with a 0.2 s recycle delay, 2048 transients. NMR spectra were Fourier transformed, phase corrected, and baseline corrected. Window functions were not applied prior to Fourier transformation. Chemical shifts were referenced relative to residual solvent peaks.

High Performance Liquid Chromatography (HPLC)

HPLC was carried on a Waters Alliance (Milford, Mass., USA) e2695 HPLC system fitted with a Waters ELSD 2424 evaporative light scattering detector. The HPLC system includes an inline degasser, a pump, and an auto-sampler. The temperature of the column (C18, 150 mm×4.6 mm, 5.0 µm, X-Bridge column, Waters Corporation, MA, USA) was maintained at 35° C. by a Waters Alliance column oven. The ELSD nitrogen flow was set at 25 psi with nebulization and drifting tubes maintained at 12° C. and 55° C., respectively. Gain was set at 500. The mobile phase was chloroform:acetonitrile (50:50)v run for 30 min at a flow rate of 0.2 mL/min. 1 mg/mL (w/v) solution of sample in chloroform was filtered through single step filter vial (Thomson Instrument Company, CA, USA) and 0.5 mL of sample was passed through the C18 column by reversed-phase in isocratic mode. All solvents were HPLC grade and obtained from VWR International (Mississauga, ON, Canada).

Differential Scanning Calorimetry

A differential scanning calorimeter (DSC) Q200 model (TA Instruments, New Castle, Del.) was used to investigate the thermal properties of the samples. The DSC measurements were carried out under a nitrogen flow of 50 mL/min. Samples of approximately 0.3 to 0.5 (±0.1) mg in a hermetically sealed aluminum DSC pan were subjected to the same thermal protocol to allow for comparison. The sample was first equilibrated at 90° C. for 10 min, a temperature and a time over which crystal memory was erased, then cooled with a constant rate (1K/min) down to −90° C., point at which the crystallization was deemed complete. The sample was held at −90° C. for 10 min then reheated to 90° C. at the same rate of 1.0 K/min to obtain the melting profiles. All measurement temperatures are reported to a certainty of better than ±0.5° C. The "TA Universal Analysis" software together with a method developed by us (Bouzidi et al., 2005) was used to analyze the data and extract the main characteristics of the peaks (peak temperature, $T_p$; onset temperature, $T_{On}$; offset temperature, $T_{Off}$; enthalpy, $\Delta H$; and full width at half maximum, FWHM). The temperature window over which a thermal event occurs is defined as the absolute value of the difference between $T_{Off}$ and $T_{On}$ of that event. The positions of non-resolved thermal events were estimated using the first and second derivatives of the differential heat flow and their other characteristics were simply estimated using the software elements.

Polarized Light Microscopy

A polarized light microscope, PLM, (Leica DM2500P, Leica Microsystems, Wetzlar, Germany) fitted with a Leica (DFC420C) digital camera was used for image capture. A Linkam LS 350 temperature—controlled stage (Linkam Scientific Instruments, Tadworth, Surrey, UK) fitted to the PLM was used to process the samples.

A small droplet of material was carefully pressed between a preheated glass microscope slide and cover-slip ensuring a uniform thin layer of sample. The sample was melted at 90° C. for 15 min to delete all crystal memory then cooled a rate of 1 K/min down to −90° C. where the sample was completely crystallized. Time resolved images (0.5 min or 0.5 C) were taken at 500× magnification starting from the liquid state until the crystallization is complete. Images of the fully crystallized material were recorded at 50×, 100× and 500× magnification.

X-Ray Diffraction

A Panalytical Empyrean X-ray diffractometer (PANalytical B.V., Lelyweg, The Netherlands) equipped with a filtered Cu-K$_\alpha$ radiation source ($\lambda$=0.1542 nm) and a PIXcel$^{3D}$ detector was used in line-scanning mode (255 lines over 3.347 degree wide detector) for XRD measurements. The XRD patterns were recorded between 1.2 and 70° (2θ) in 0.0131° steps, at 45 kV and at 40 mA. The procedure was automated and controlled by PANalytical's Data Collector (V 3.0c) software. The samples were processed in the XRD chamber using a 700 Series Cryostream Plus cooling system (Oxford Cryosystems, Oxford, UK) fitted to the diffractometer. The sample was heated to 80° C., hold at that temperature for 5 min to delete all crystal memory then cooled down to −60° C. at a rate of 1 K/min. The temperature was controlled to better than ±0.5° C. The data were processed and analyzed using X'Pert HighScore V3.0 software (PANalytical). We refer to the range 2θ=[0.3-15]° and [15-70]° as the small- and wide-angle scattering regions, respectively.

Synthesis and Characterization of the Dimer

The synthesis route of the dimer is shown in Scheme 2. Compound D was prepared from 1-oleyol-3-stearoyl-2-hydroxyl propane (2) and 1,18-Octadec-9-enedioic acid (3). 1-oleyol-3-stearoyl glycerol (2) was synthesized from 2,3-dihydroxypropyl oleate (1) and stearoyl chloride in the presence of pyridine.

Scheme 2. Synthesis route of (E)-1-(1-(oleoyloxy)-3-(stearoyloxy)propan-2-yl) 18-(1-(oleoyloxy)-3-(stearoyloxy)propan-2-yl) octadec-9-enedioate (Compound D).

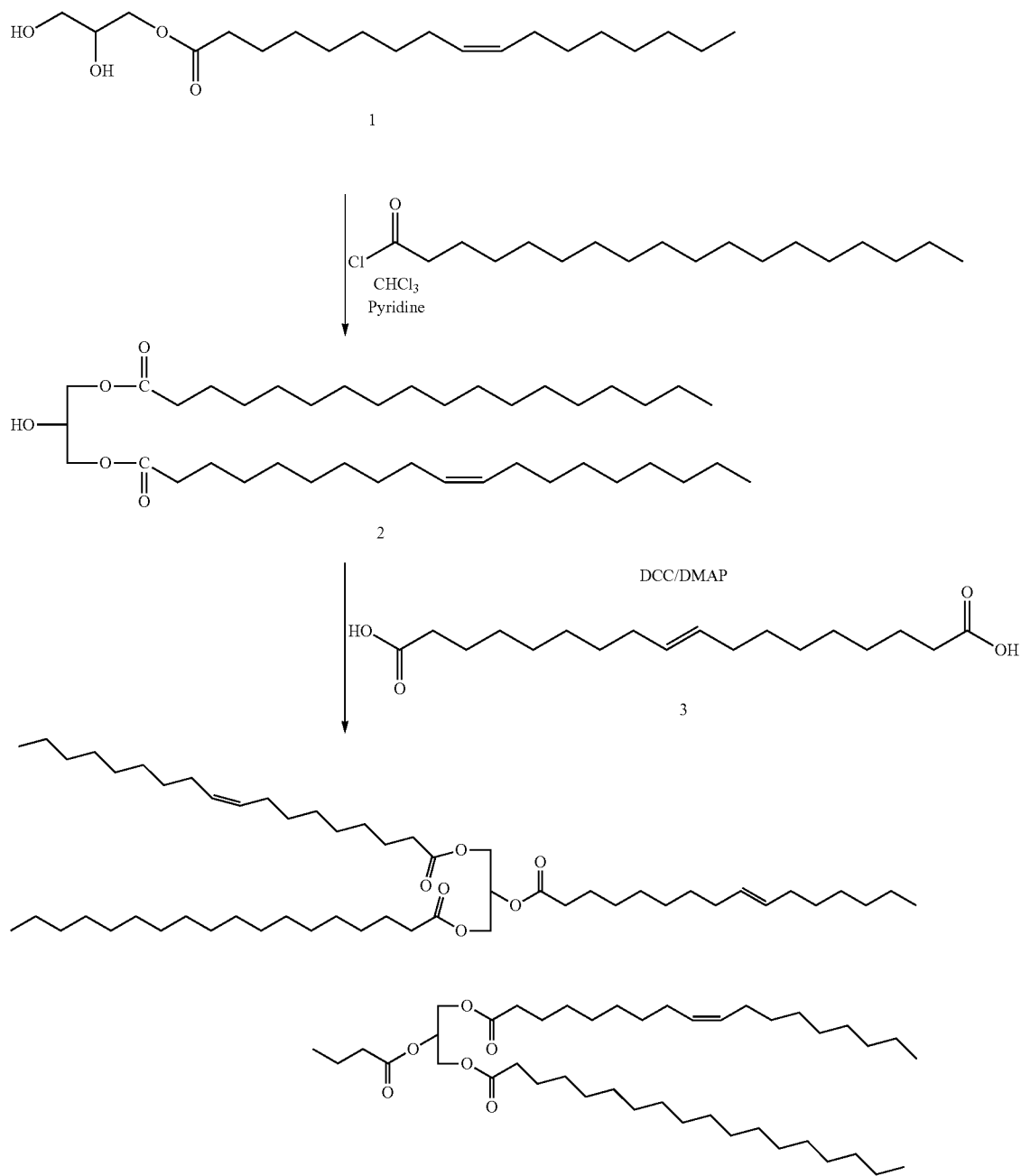

Synthesis of 1-oleyol-3-stearoyl-2-hydroxyl propane (2)

To a solution of (32.4 mmol) 2,3-dihydroxypropyl oleate (1) in 200 mL chloroform, stearoyl chloride (32.4 mmol) was added. Then (48.6 mmol) pyridine was added to reaction solution drop wise. The reaction mixture was stirred at room temperature overnight. The reaction mixture was diluted with another 160 mL chloroform. The organic layer was washed with water (3×300 mL), followed sequentially by 5% HCl (2×300 mL), water (2×300 mL), 4% NaHCO$_3$ (2×300 mL), water (3×300 mL). The organic layer was dried on Na$_2$SO$_4$. After chloroform was removed, the residue was purified by column chromatography with hexanes/ethyl acetate=20:1.

Yield: 73%

$^1$H-NMR (in CDCl$_3$, ppm): 5.34 ppm (2H, m), 4.18-4.14 ppm (4H, m), 2.36-2.33 ppm (4H, t), 2.02-2.00 ppm (4H, t), 1.62 ppm (4H, m), 1.34-1.26 ppm (46H, m), 0.88 ppm (6H, t).

Synthesis of (E)-1-(1-(oleoyloxy)-3-(stearoyloxy) propan-2-yl) 18-(1-(oleoyloxy)-3-(stearoyloxy)propan-2-yl) octadec-9-enedioate (Compound D dimer)

To a solution of (1 mmol) 1-oleoyl-3-stearoyl-2-hydroxyl propane (2) and (1 mmol) diacid in 10 mL $CHCl_3$ under the protection of $N_2$, 0.2 mmol DMAP was added, followed by 1.2 mmol DCC. The reaction was carried out at room temperature overnight. The precipitated dicyclohexylurea was removed by filtration. The organic phase was diluted with 10 mL chloroform, then washed sequentially with water (3×20 mL), 4% aqueous $NaHCO_3$ (2×200 mL) and brine (3×200 mL), and then dried over $Na_2SO_4$. After filtration, the filtrate was concentrated with a rotary-evaporator and the residue was purified by column chromatography with ethyl acetate/hexanes=1:20.

$^1$H-NMR (in $CDCl_3$, ppm): δ=5.36-5.30 (6H, m, —C$\underline{H}$=C$\underline{H}$—), 5.24 (2H, m, —CH$_2$C$\underline{H}$(O)CH$_2$—), 4.28-4.25 (4H, dd, —CH(O)C$\underline{H}_2$O—), 4.14-4.10 (4H, dd, —CH(O)C$\underline{H}_2$O—), 2.31-2.27 (12H, t, —OOCC$\underline{H}_2$CH$_2$—), 2.01-1.92 (12H, m, —CH=CHC$\underline{H}_2$CH$_2$—), 1.63-1.60 (12H, m, —OOCCH$_2$C$\underline{H}_2$—), 1.30-1.27 (112H, m, —C$\underline{H}_2$—), 0.90-0.86 (12H, t, —C$\underline{H}_3$);

$^{13}$C-NMR (in $CDCl_3$, ppm): δ=173.28, 172.84, 130.26, 129.99, 129.69, 68.85, 62.07, 34.18, 34.03, 34.03, 32.58, 31.91, 29.75, 29.69, 29.65-29.05, 27.20, 27.16, 24.85, 22.67, 14.10.

Yield: 70.9%.
Purity: 99.9%

Results and Analysis—Crystal Structure

The WAXD spectra of the mixture with $X_D$≤0.10, 0.50$_D$ and MeP are shown in FIG. 1a. The relevant d-spacings and Miller indices are reported in Table 1. One can see that only the orthorhombic form (β'-polymorph) was detected as shown by its characteristic ($\bar{1}$10) and (200) reflections (Table 1). The appearance of a doublet (4.04 Å (020) and 4.10 Å ($\bar{1}$10)-lines) for the mixture with $X_D$≤0.10 indicates that more than one β'-phase was involved in the crystallization of these mixtures. As can be seen in FIG. 1a, the MeP phase as represented by the intensity of its signature peak (4.40 Å) almost disappeared as soon as Compound D was added. The 4.40 Å peak decreased sharply and retained only a 10$^{th}$ of its initial value for the 0.025$_D$ mixture. It remained very weak for the mixtures measured and did not appear for Compound D nor for 0.50$_D$, indicating that a very small pure MeP phase persisted only for the mixtures with the lowest Compound D content. The disappearance of the MeP phase is confirmed by the similar and more noticeable decrease, if not disappearance, of the most intense line of pure MeP (line 3.67 Å, FIG. 1a). This line was 40 times higher than the (200) line observed at 3.65 Å in mixtures containing Compound D ($X_D$≥0.025). This indicates that despite such close positions, the two lines did not originate from the same phase. The latter is tied principally to phases involving Compound D. A very small MeP phase, however, may be still represented with a very weak superimposed peak.

The intensity of the (200) line increased practically exponentially from 0.025$_D$ to 0.10$_{D3}$ and dropped to a third of its value for $X_D$ indicating that it can be safely attributed to a Compound D phase. The 4.28 Å-line which appeared only for the mixtures, and not for any of the pure components, increased also exponentially supporting the presence of a Compound D/MeP mixed phase whose content increased with increasing Compound D. Both the 4.04 Å- and 4.10 Å-lines increased with increasing $X_D$ but at a different rate. The 4.04 Å (020) line increased much more rapidly than the 4.10 Å ($\bar{1}$10) line and did not appear for Compound D. The 4.10 Å line increased exponentially to a maximum for D ($R^2$=0.9958; critical Compound D molar ratio of 0.30). The peculiar variation with $X_D$ of these two lines provide further support for the presence of a Compound D/MeP mixed phase in the mixtures having a Compound D molar ratio lower or equal to 0.10. It indicates that while the 4.10 Å line may be associated with a Compound D family of planes, the 4.04 Å originated from a mixed phase, adequately located at the (020) position, i.e., the center of the subcell.

Figure 1B:
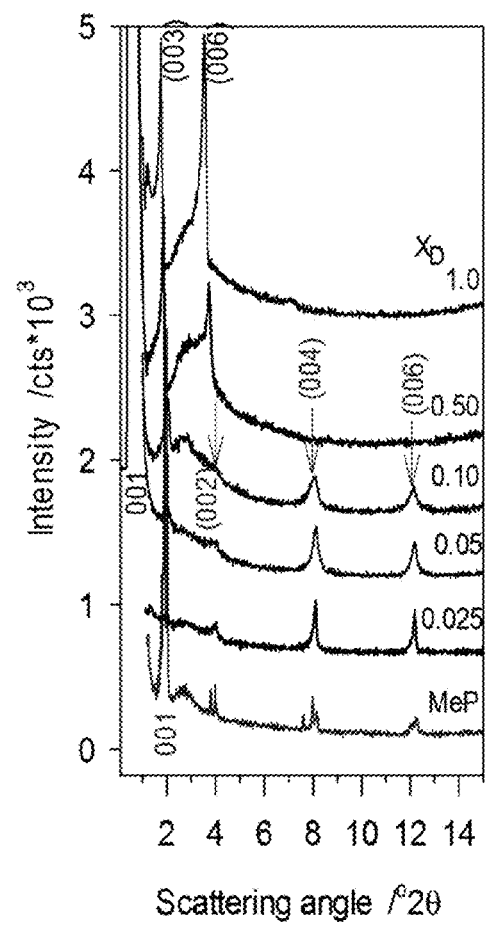

The small angle diffraction spectra are shown in FIG. 1b and the corresponding SAXD data are listed in Table 1. These data stress the peculiarity of the packing of the mixtures having a Compound D molar ratio equal or less than 0.10$_{D3}$ and the predominance of a Compound D-type of packing for all the others. The mixtures having $X_D$≤0.10 displayed a chain length repeat unit (43.50±0.51 Å) very close to that of MeP (43.99 Å). The chain stacking of the mixtures was probably guided by the pure MeP chains which accommodated the packing of the more bulky Compound D molecules. Three MeP molecules would be necessary to accommodate one dimer. Note that the harmonics which showed are all even. The very large disorder suggested by the (exponential) decrease of the already very weak intensity of the (004) and (006) reflections with increasing Compound D content from 0.025 is worth noting. Note also that the (001) lines obtained for the mixture widened with increasing Compound D content indicating a small coherence length, a clear sign of very small crystals.

The repeat unit of the chain packing of Compound D ($d_{001}$=149.10 Å) and all mixtures with $X_D$>0.10 is three times larger than those for mixtures with $X_D$<0.10. This length can accommodate three dimers stacked along the c-axis. The fact that only the odd harmonics were present indicates that the nature of the packing is different from the packing initiated by MeP and suggests that units of Compound D/MeP are the building blocks of the chain packing.

TABLE 1

Wide and small angle x-ray diffraction data. Miller indices are those of the orthorhombic crystal structure (β'-form).

| $X_D$ | (110) | ($\bar{1}$10) | (020) | (200) |
|---|---|---|---|---|
| 0.0 | 4.39 | | 4.08 | 4.06 | 3.67 |
| 0.025 | 4.42 | 4.28 | 4.09 | 4.03 | 3.65 |
| 0.05 | 4.39 | 4.27 | 4.09 | 4.03 | 3.64 |
| 0.10 | 4.39 | 4.29 | 4.09 | 4.04 | 3.65 |
| | 4.40 ± 0.01 | 4.28 ± 0.01 | 4.09 ± 0.01 | 4.03 ± 0.01 | 3.65 ± 0.01 |
| 0.50 | NA | NA | 4.10 | NA | 3.66 |
| 1.0 | NA | NA | 4.13 | NA | 3.68 |

| $X_D$ | 001 | 002 | 004 | 006 |
|---|---|---|---|---|
| 0.0 | 43.99 | 21.81 | 10.88 | 7.25 |
| 0.025 | 42.96 | 21.85 | 10.88 | 7.25 |
| 0.05 | 43.86 | 21.95 | 10.88 | 7.27 |
| 0.10 | 43.19 | 22.30 | 10.95 | 7.29 |
| | 43.50 ± 0.51 | 21.98 ± 0.22 | 10.89 ± 0.03 | 7.26 ± 0.01 |

| | 001 | 003 | 006 | 0012 |
|---|---|---|---|---|
| 0.50 | 142.71 | 47.26 | 23.60 | |
| 1.0 | 149.10 | 49.50 | 24.85 | 12.47 | — |

Crystallization Behavior

Figure 2B:
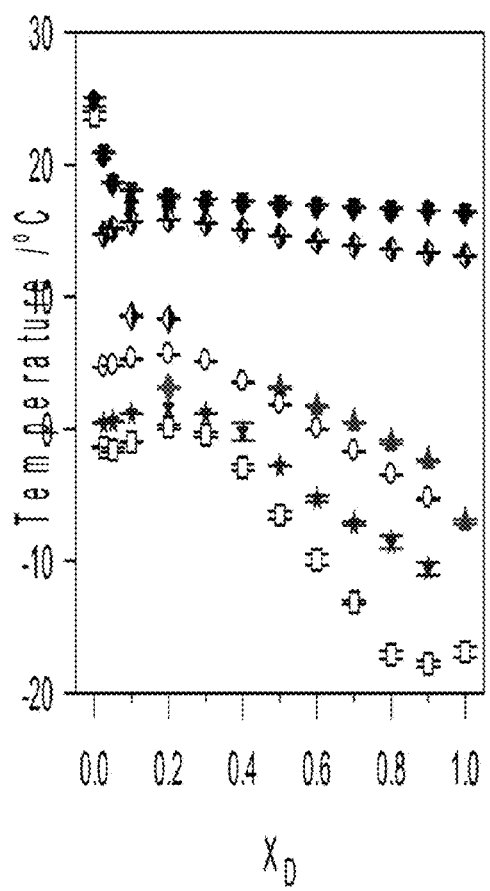
FIG. 2B depicts kinetic phase diagram obtained using the characteristic transition temperatures obtained during cooling.

The DSC cooling thermograms are displayed in FIG. 2a and the corresponding characteristic temperatures in FIG. 2b. The thermograph of pure MeP shows one main peak at ~24° C. (P1 in FIG. 2a), and that of pure Compound D presented two relatively large peaks at ~16° C. and 13° C., and a small peak at −7.03±0.17° C., indicative of the occurrence of three different phase transitions during the crystallization process. The addition of Compound D to MeP was marked by a noticeable extra peak at the high temperature side of the thermogram (P2, FIG. 2a1), and twin peaks (P3 and P4, FIG. 2a3) at the low temperature side of the thermograms. Note that a resolved peak clearly appeared between P1 and P2 for the $0.10_D$ and $0.20_D$ mixtures, and at least one non-resolved peak can be observed between P1 and P2 for the other mixtures. As Compound D concentration was increased, P1 shifted to lower temperature, noticeably first (−69.9±23.1 K/mol) to 17.20±0.05° C. at $X_D$=0.15, then very gradually (−1.2±0.1 K/mol) to 16.16±0.07° C. for $X_D$=1.0 (FIG. 2b). A similar trend was observed for the small twin peaks P3 and P4. Obviously, the effect of Compound D on MeP onset of crystallization was optimum at the low $0.15_D$ concentration. The peak appearing closest to the MeP exotherm (P2 in FIG. 1a) grew larger and closer to P1 up $0.15_D$ at which point it shifted back to lower temperature.

Figure 2C:
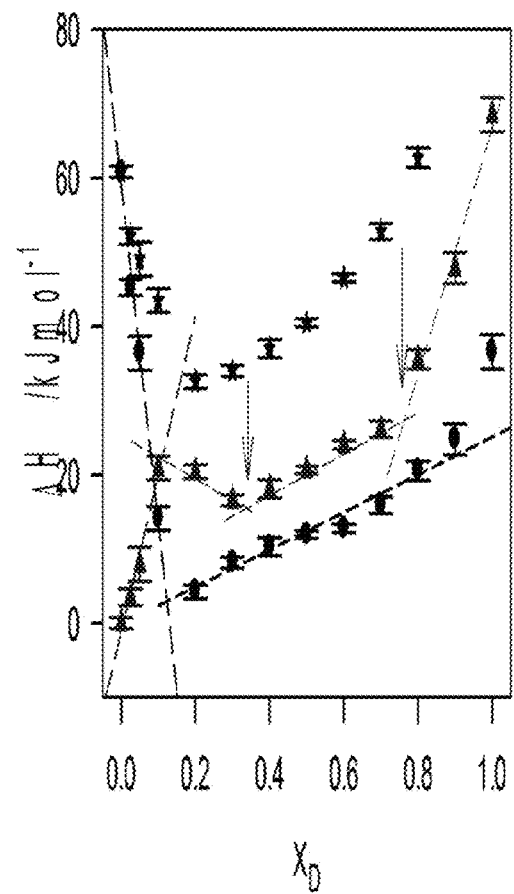
FIG. 2C depicts enthalpy of crystallization of peaks P1 (●, $\Delta H_1$), P2 (▲, $\Delta H_2$) and total enthalpy of crystallization (★, $\Delta H_c$).

A plot of the enthalpy of the individual peaks (FIG. 2c) presented a typical Tamman triangle with a base from $X_D$=0 to 0.30 and peaking at $\sim X_D$=0.15, indicating a particular reaction, possibly a eutectic transformation. The same plot shows two other singularities at $X_D \sim 0.40$ and $X_D \sim 0.75$ (arrows in FIG. 2c), which may be related to particular reactions. The enthalpy of the twin peaks (P3 and P4) also presented Tamman-like plots (not shown) with the triangle peaking at $X_D$=0.30 for both peaks, indicating that the reactions implicating the low temperature phases of Compound D are different from those involving the phases at higher temperature. Since Compound D presented only one of these peaks, one can validate that at least one of the twin peaks, if not both, is associated with a mixed Compound D/MeP phase. It is interesting to note that even if the peak positions of the Compound D thermogram are slightly shifted to higher temperature with increasing MeP content, the overall shape of the thermogram of Compound D did not change noticeably up to $0.10_D$, as if MeP molecules merged within this oligomer by packing on its different branches. A possible scenario for the crystal packing for the Compound D-rich mixtures is the alignment of MeP with the saturated branches, and with the C18 trans-bridge of the dimer, yielding a relatively loose buildup of Compound D-MeP units, having 1 to 3 MeP straight chains each. The relative diversity of these units, while allowing for a slight change in crystallization temperature (the higher MeP concentration, the higher the onset of crystallization), would not change the overall transformation path of the Compound D molecules. It appears as if Compound D was the carrier of MeP molecules through the melt in forming the phases that form for the mixture with Compound D concentrations higher than 15%. This parasitic-like association must have occurred in the liquid phase promoted by unhindered Compound D chain rotations, and favorable MeP diffusion and easy mass transfer.

The noticeable change in the peak temperature of P1 (MeP peak) which occurred for the mixtures having a concentration of Compound D between 0.00 to 0.2, indicates that Compound D perturbs the packing of MeP via its two cis-branches because there is not enough Compound D molecules to accommodate all the MeP chains to act as a unit. This may be explained by a growing tendency of the MeP molecules to form lamellae rather than associate with Compound D due to mean free path considerations.

Note that the shape of the thermograms of the $0.10_D$ and $0.20_D$ mixture are also reminiscent of Compound D, suggesting that the D/MeP "parasitic" association was ongoing for some of the Compound D molecules even at very low MeP content. The competition between MeP lamellae formation and association mechanisms seems to have been most active for the mixtures between $0.40_D$ and $0.10_D$, included, as suggested by the relative changes observed in the shape of P1 and P2, and the events between them.

The interesting variation of the intensity of the different peaks show that such a packing is possible. MeP may be the interstitial molecule that is probed by the 020 reflection of the orthorhombic cell, the only crystal form detected by XRD for all the mixtures. Furthermore, the value of the 001d-spacing (50 Å) for Compound D and the Compound D-rich mixtures can account for the packing of the units made of the "associated" MeP in Compound D. The peculiar variation of the intensity of the 4.04 and 4.10 peaks in the [0.00 to 0.2] concentration range may be related to the balance between MeP lamellar formation and MeP—Compound D association.

Melting Behavior and Phase Development

The heating thermograms of the Compound D/MeP binary system are relatively complex (FIG. 3a1-3). The phase development inferred from the heating cycles depends strongly on Compound D concentration. It fully mirrors that as determined from the cooling cycles. Several polymorphic transformations appeared as soon as Compound D was added to MeP as can be seen in the heating thermogram of the $0.025_D$ mixture (FIG. 3a1) which presented four extra peaks compared to pure MeP. Overall, one can single out three major events in the [10-35]° C. range of temperature (P1, P2 and P3 in FIG. 2a2). P1 which appeared for MeP decreased noticeably with increasing Compound D concentration and disappeared for mixtures with $X_D$>0. P2 appeared for $0.025_D$ and all mixtures whereas, P3 was only observed from the $0.30_D$ concentration onwards. Also, similarly to the cooling thermograms, twin peaks are observed in the heating thermograms (P3 and P4 in FIG. 3a3), and are probably the recording of the melting of the phases crystallized at low temperature and represented by the twin exotherms observed in the cooling cycles (P3 and P4 in FIG. 2a3). P1 was followed by a wide exothermic peak centered at ~25.24±0.86° C. for the mixtures with $X_D$≥0.10. The exotherm was followed by two endotherms indicating that two phases of higher stability have recrystallized from the melt. Note that the enthalpy of the exotherm was exactly the same as that of the following endotherms (FIG. 3c), indicating that these latter phases recrystallized separately and are probably in the same crystal form, but made of different constituents. The nature and composition of these two phases are out of the scope of the present effort.

The complexity of the transformation behavior of the Compound D/MeP binary system is well represented by the phase diagram constructed using the peak temperature of the resolved peaks detected in the heating cycles of the Compound D/MeP mixtures shown in FIG. 3b. The liquidus line in the phase diagram obtained using the offset of melting of the Compound D/MeP mixtures is noteworthy. It displays a minimum at $0.05_D$, suggesting an apparent eutectic and a singularity at $0.40_D$, two plateaus ($T_{off}$=35.9±0.1° C. from $0.15_D$ to $0.30_D$ and $T_{off}$=43.4±0.2° C. from $0.50_D$ to $0.70_D$) and a linear increase for the Compound D-richer mixtures. The flat liquid-solid transformation line in each plateau represents the melting of the same stable crystal phase, probably with the same constituents. The jumps in melting temperature observed at $0.10_D$, $0.40_D$ and $0.70_D$ indicates the stepped increase in the stability of the available crystal forms with increasing Compound D content. It is noteworthy that a well-defined, most stable phase is available in a well-defined concentration range of the Compound D/MeP system. The discontinuous ordering of the phases available is a strong indicator of the inertia of the bulky dimer and the increase of stability with increasing Compound D content, particularly after $0.70_D$, highlights that Compound D is ultimately driving the phase behavior of the D/MeP binary system.

The kinetic phases of this binary system can be located below the offset temperature of melting ($T_{off1}$, ▼ in FIG. 3b) of the main melting peaks (P2 and P3 in FIG. 3a). As can be seen in FIG. 3b, the melting temperature of these phases gradually decreased until the $0.50_D$ mixture where it plateaued. Note that the $T_p$ of the peaks below $T_{off1}$ also plateaued at $0.50_D$. The transformations described by these peaks are solid-solid transformations which can be explained by the relatively easier diffusion of MeP molecules between the fatty acid chains of the bulky Compound D. The plateau may be understood if one considers that after the 50% mixture, this diffusion is noticeably limited by larger interaction hindrances by Compound D.

The enthalpy of P1 decreased very noticeably while that of P2 showed a Tamman —like maximum at $0.20_D$, plateaued for $0.30_D$ to $0.70_D$ then increased again to reach its maximum for the pure Compound D (FIG. 3c). The endotherm, P3, which appeared at $0.30_D$ also increased almost linearly to reach a maximum for the pure Compound D. The maximum observed in Tamman plot at $0.20_D$ did not match the apparent eutectic observed in the liquidus line at $0.05_D$ suggesting that the reaction may not be of a more complex nature than a simple eutectic.

Microstructure

Figures 5A, 5B:
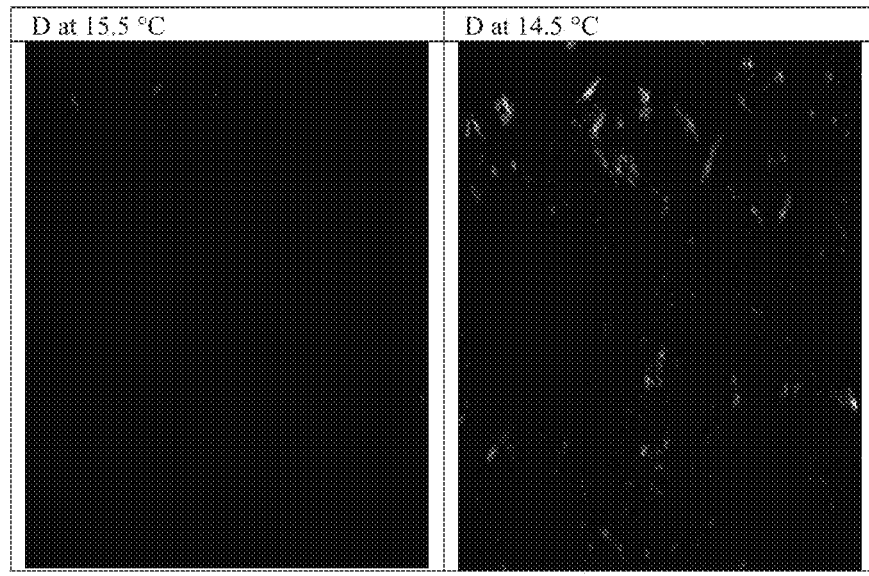
FIGS. 5A, 5B, 5C, and 5D depict PLM images (500×) of the pure dimer Compound D obtained at selected temperatures after cooling from the melt at a constant rate of 1 K/min.
Figures 5C, 5D:
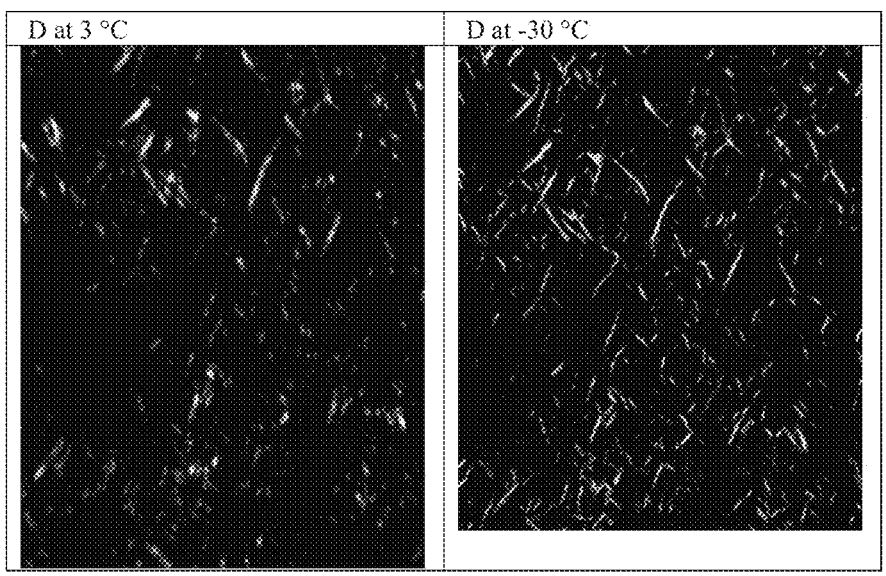
Figures 6A, 6B, 6C:
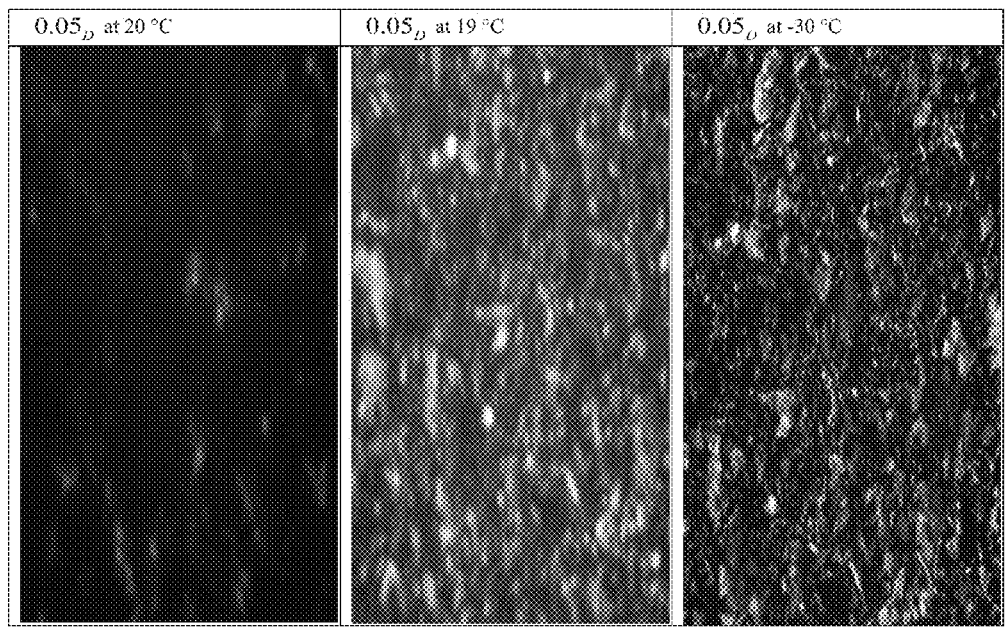
FIGS. 6A, 6B, and 6C depict PLM images (500×) of $0.05_D$ mixtures obtained at selected temperatures after cooling from the melt at a constant rate of 1 K/min.

To better understand the microstructural changes, two mixtures ($0.05_D$ and $0.10_D$) were chosen to be studied in more detail. The characterization of pure Compound D and MeP crystals provide a baseline for comparison. Multi time PLM measurements were performed during the crystallization of the samples. The first crystals of pure Compound D appeared at 15.5° C. as small entities (FIG. 5a) which continued to grow into relatively long platelet-like crystals (FIG. 5b). The rate at which new crystals appeared was relatively low as it took approximately 12 min (corresponding to 12° C.) to fill the PLM slide. This temperature window can be related to the width of the main two exotherms shown by the cooling DSC thermogram of this compound. The final microstructure ended up as a dense fibrillar network (FIG. 4a). The crystal network of the $0.05_D$ sample started with several bright spherulitic crystallites at 20° C. (FIG. 6a). These increased and grew very rapidly (~19° C.) into a network of large aggregates in which smaller structures, platelet-like crystals and a few Maltese crosses, are observed (FIG. 6b). This indicated the presence of multi-lamellas. The network evolved only towards better aggregation and resolution for the small entities without fundamentally changing the shape of the microstructure (FIG. 4b). Understandably, the onset temperature of crystallization for these two samples is a little higher than the corresponding $T_{On}$ measured by DSC (~1° C. earlier), as this latter is not taken at the deviation of the DSC signal from the baseline, but at the intersection of the baseline with the steepest slope of the signal.

Figures 7A, 7B:
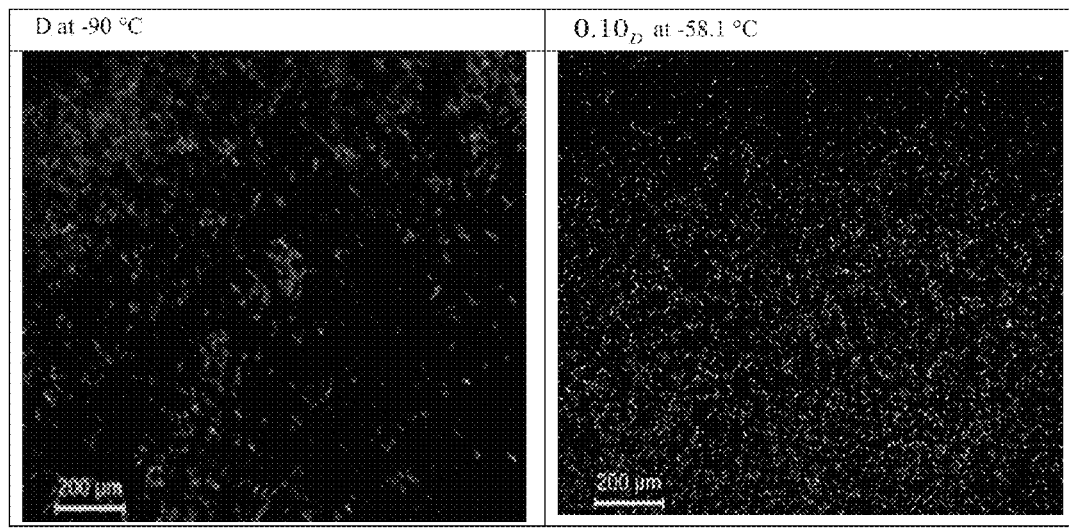
FIGS. 7A and 7B depicts PLM images (100×) of fully crystallized Compound D (7a) and a $0.10_D$ mixture obtained after cooling from the melt at a constant rate of 1 K/min (7b).

The crystals of the $0.05_D$ mixture continue to grow and form aggregates, as shown in the sample image taken at 19° C. (FIG. 6b). The $0.10_D$ sample showed its first crystals at 18.3° C. and presented nucleation and growth behaviors similar to Compound D (FIG. 7). It also formed a homogenous fibrillar network similar to Compound D (FIG. 4c). However, the microstructure of $0.10_D$ is relatively denser than that of Compound D and its fibrils smaller. The microstructure of the $0.05_D$ mixture is in stark contrast to those of $0.10_D$ and pure Compound D, as well as MeP. MeP microstructure which formed very rapidly into a very large radially growing leaflet-like crystallite (FIG. 4c) lost its characteristics and shape as soon as Compound D was added to it, outlining the noticeable effect of Compound D on the growth of the FAME at very small loading.

The microstructure shown by these mixtures may be related to their DSC melting traces. The mixture which presented a dominant MeP peak (P1 in FIG. 3a1) have probably grown a large MeP dominant phase, which showed as the large aggregates in pure MeP and $0.05_D$. The noticeable decrease of P1 and concomitant increase of P2 (FIG. 3a1), the representative of a phase dominated by Compound D, can explain the disappearance at very low concentration of the large aggregates observed in the $0.05_D$ sample and the predominance of the fibrillar entities, representative of a Compound D microstructure. Note that P1 did not completely disappear for the $0.10_D$ sample, but is small enough to explain why no aggregate was observed under the PLM for this mixture. The DSC data for mixture with more than $0.40_D$ show a clearly defined extra peak (P3 at approximately 15-16° C.) besides the transitions between approximately 20-25° C., in addition to the clearly defined peak corresponding to the melting of Compound D (FIG. 3a2). The microstructure of the phase associated with the P3 melting peak is very similar to that of pure Compound D, because even with the substantial increase of P3 enthalpy with increasing Compound D content, no change from the microstructure of Compound D has been observed in the PLM of any of the mixtures where P3 was detected. The intermediate DSC peak shown in the DSC melting traces of samples with 2.5 to 20% Compound D content between the Compound D and MeP melting peak (at approximately 20 to 25° C., FIG. 3a1) are probably mixed phases hypothesized to act as linking domains between the Compound D and MeP crystals.

As a general recap, the phase behavior of a model binary system made of methyl palmitate (MeP) and (E)-1-(1-(oleoyloxy)-3-(stearoyloxy)propan-2-yl) 18-(1-(oleoyloxy)-3-(stearoyloxy)propan-2-yl)octadec-9-enedioate (Compound D), a triacylglycerol dimer which can be produced safely and inexpensively by metathesis of natural oil, was investigated using DSC, XRD and PLM. The XRD data evidenced that the solid phases formed after a relatively slow cooling (1 K/min) were in the orthorhombic crystal symmetry. The crystal packing was shown to be guided by the bulky Compound D molecules at concentration levels as low as 10%.

The phase diagram obtained using the DSC cooling traces presented a singularity at the 10% mixture for all the characteristic transition temperatures. At this level of loading, the onset of crystallization of MeP was reduced by 5-6° C. For richer mixtures, Compound D had practically no apparent effect on the induction of crystallization. The typical Tamman triangle presented by the enthalpy of the individual peaks indicated a particular reaction at $\sim X_{D3}=0.15$ confirming the possible eutectic displayed in the liquidus line of the cooling phase diagram. The same plot showed two other singularities at $X_{D3}\sim0.40$ and $X_{D3}\sim0.75$, which may be related to particular reactions which were not detected in the liquidus line for kinetic reasons.

The phase diagram of this system constructed using the DSC heating data was very complex and unusual. It has been found that beyond the apparent eutectic formed at about 5% of Compound D, the most stable phases available for the system form in three defined steps of increasing stability. On the other hand, the melting temperature and stability of kinetic phases decreased steadily to plateau at the 50% mixture. The findings are explained by the formation beyond 10%, of Compound D/MeP associated units in which the dimer carries the MeP molecules on its fatty branches and bridge starting from the liquid state where mobility of MeP and free rotation of the Compound D branches are favorable. The disruptive effect of Compound D on the packing of the saturated FAME was effective only at low concentrations (<0.15) because there is not enough Compound D carriers to form the Compound D/MeP composite units. The arrangement in units of a linear molecule whose size is comparable to the fatty branches of the bulky structure with which it was mixed is consistent with the DSC as well XRD data.

The foregoing detailed description and accompanying figures provided a fundamental understanding of how Compound D may be used as an effective crystallization depressant that can delay crystal nucleation and growth, and reduce crystal size at concentrations of less than 5%. Moreover, the foregoing detailed description and accompanying figures have been provided by way of explanation and illustration, and are not intended to limit the scope of the invention. Many variations in the present embodiments illustrated herein will be apparent to one of ordinary skill in the art, and remain within the scope of the claims and their equivalents.

What is claimed is:

1. A biodiesel crystallization depressant composition comprising a triacylglycerol dimer, which is (E)-1-(1-(oleoyloxy)-3-(stearoyloxy)propan-2-yl) 18-(1-(oleoyloxy)-3-(stearoyloxy)propan-2-yl)octadec-9-enedioate, mixed with a biodiesel fuel.

2. The composition of claim 1, wherein the biodiesel fuel comprises methyl palmitate.

3. The composition of claim 2, wherein the triacylglycerol dimer and methyl palmitate are mixed to a molar fraction, $X_D$, where X ranges from greater than 0 to 1.0.

4. The composition of claim 3, wherein the mixture of triacylglycerol dimer and methyl palmitate comprises a binary phase behavior comprising one or more eutectics.

5. The composition of claim 3, wherein the mixture of triacylglycerol dimer and methyl palmitate comprises a eutectic at molar fraction $0.05_D$.

6. The composition of claim 3, wherein the mixture of triacylglycerol dimer and methyl palmitate, comprises a maximum depression of crystallization onset at molar fraction $0.10_D$.

7. The composition of claim 3, wherein the mixture of triacylglycerol dimer and methyl palmitate, comprises the optimum exhibit of crystal packing at molar fraction $0.15_D$.

8. The composition of claim 3, wherein the mixture of triacylglycerol dimer and methyl palmitate comprises a singularity at approximately $0.40_D$ and $0.75_D$.

9. The composition of claim 1, wherein the triacylglycerol dimer comprises an onset of crystallization at 15.5° C.

10. The composition of claim 3, wherein the mixture of triacylglycerol dimer and methyl palmitate, comprises an onset of crystallization at 20° C. where the molar fraction is at $0.05_D$.

11. The composition of claim 3, wherein the mixture of triacylglycerol dimer and methyl palmitate, comprises an onset of crystallization at 18.3° C. where the molar fraction is at $0.10_D$.

* * * * *